United States Patent [19]

Turi et al.

[11] Patent Number: 5,895,380
[45] Date of Patent: Apr. 20, 1999

[54] ABSORBENT PRODUCTS

[75] Inventors: Mordechai Turi; Pramod S. Mavinkurve, both of Princeton; Linda J. McKeekin, Bound Brook, all of N.J.

[73] Assignee: McNeil-PPC, Inc., Skillman, N.J.

[21] Appl. No.: 08/801,243

[22] Filed: Feb. 19, 1997

Related U.S. Application Data

[63] Continuation of application No. 08/522,772, Sep. 1, 1995, abandoned.

[51] Int. Cl.⁶ .................................................. A61F 13/15
[52] U.S. Cl. ........................ 604/383; 604/378; 428/107; 428/109; 428/131
[58] Field of Search ........................... 604/358, 367, 604/370, 372–373, 378–380, 383–385.1; 428/107, 109, 131, 137, 141, 147, 274

[56] References Cited

U.S. PATENT DOCUMENTS

| | | | |
|---|---|---|---|
| 4,397,644 | 8/1983 | Matthews et al. | 604/378 |
| 4,685,914 | 8/1987 | Holtman | 604/367 |
| 4,846,823 | 7/1989 | Enloe | 604/358 |
| 4,900,320 | 2/1990 | McCoy | 604/387 |
| 5,308,346 | 5/1994 | Sneller et al. | 604/387 |

FOREIGN PATENT DOCUMENTS

| | | | |
|---|---|---|---|
| WO 93/15701 | 8/1993 | WIPO | 604/370 |

*Primary Examiner*—Robert A. Clarke

[57] ABSTRACT

This invention provides absorbent products, having a permeable cover made of a microperforated fibrillated thermoplastic film that has improved properties such as intimate, but nonoccluding contact with the body, yet providing comfort and resilience and immediate fluid acceptance and distribution. The cover is characterized by having non perforate regions and perforate regions, the perforate regions having a plurality of microholes defined by a network of fiberlike elements, the perforate regions being, at least in part, at elevations that are higher than the nonperforate regions. The perforate regions are caused to be at higher elevations by methods such as tensioning the cover or by partly adhering the cover to the absorbent body of the product or by combinations thereof. The microholes may be of different sizes and shapes. One embodiment provides an absorbent product having a cover with apertures larger than microholes, alone or in addition to microholes, and greater open area, so that viscous fluids such as menses can readily flow through, the cover having for example at least one group of large apertures or at least two different size groups of apertures. Additional improvement of fluid acceptance and distribution properties is obtained by corona discharge treatment of one side of the film before microperforating and by treating the microperforated film with surfactant.

48 Claims, 5 Drawing Sheets

ABSORBENT PRODUCTS

This is a continuation of application Ser. No. 08/522,772, filed Sep. 1, 1995, now abandoned.

FIELD OF THE INVENTION

The present invention relates generally to absorbent products such as sanitary napkins, diapers, incontinence products, surgical dressings, underpads and the like; and particularly to absorbent products that are able to immediately capture bodily fluids such as menstrual fluid, urine and wound exudate, to transfer such fluid away from the body and from the point of contact of the product with the body and to subsequently distribute and retain the fluids within the product. This invention also relates particularly to absorbent products that can manage bodily fluids as described above, while adapting to the complex contours of the body, and maintaining close, but comfortable, resilient and cool comfort for the user. This invention also particularly relates to absorbent products that maintain a quality appearance even after being folded for packaging, by springing open ready for use and by only minimally retaining creases of the folds that tend to disrupt the integrity of the absorbent materials of the product and that promote leakage along the paths of the folds.

Absorbent products in the past have been provided with perforate covers that are made of such materials and with perforations of such design so that the covers may effectively receive and transfer fluids away from the body. Early perforate covers were made of woven and knitted materials some of which were of inherently wettable materials such as cotton and rayon. While these wettable materials absorbed the fluid readily, they did not readily release it to the absorbent structures below and thereby exhibited what is termed "wetback", wherein the fluid continues to wet the body with which it is in contact. Nonwettable materials such as polypropylene and polyester replaced these inherently wettable materials. To lend the nonwettable materials some degree of wettability, so that fluid acceptance and transfer could occur readily without compromising resistance to wetback, the nonwettable covers were treated with fugitive wetting agents, such as surfactants, and with nonfugitive wetting agents such as wettable polymers.

The woven and knitted materials were substantially replaced by nonwoven fabrics and by perforated films for purposes of economy and the need to engineer in specific functional designs such as three dimensionality and reduced wetback. Although nonwoven fabrics could be made with three dimensional almost woven or knitted appearance, e.g., hydoentangled nonwovens, their appearance and function was for the most part that of flat paperlike materials that still suffered from wetback.

Perforated films were made by methods such as by: embossing and then stretching the thinned areas, that are embossed into plastic films, until the thinned areas are burst open—as described in U.S. Pat Nos. 4,690,679 and 4,806,411 to Mattingly et al and in U.S. Pat. No. 4,859,519 to Cabe et al. Perforated films were also made: by applying pressure to a plasticized thermoplastic film on a perforated support or molding element, as in U.S. Pat. No. 3,054,148 to Zimmerli; by vacuum perforating, where hot air is drawn through a film that is supported on a perforated drum through which a vacuum is drawn; by pin perforating; by perforating by means of energy sources such as ultrasound, laser and high energy radiation and by chemical means such as leaching out aqueous or nonaqueous solvent soluble particles. Such perforated films, being essentially flat on the body contacting side and having only minor surface features, also suffered from the same drawbacks as did nonwoven fabrics.

It was found, e.g., U.S. Pat. No. 3,929,135 to Thompson et al and U.S. Pat. No. 4,324,246 to Mullane, that perforated films, being somewhat more moldable than nonwovens, could be given a three dimensional look, by creating three dimensional structures having entry and exit orifices, such as funnel like structures, that have orifices at the film surface and smaller orifices at exits located at the end of protrusions that extend below and beyond the film surface. Such perforated films were created, for example, by vacuum perforating or by mechanically perforating a film that is supported on a surface of a die having three dimensional tapered structures with holes at either end thereof. The film is thereby forced to take the shape, e.g., a funnel, of the die's three dimensional structure; the position of the entry orifice of the three dimensional structure in the film being coplanar with the film's surface and the position of the exit orifice of the three dimensional structure in the film being dictated by the location of the exit hole in the die, usually at the bottom. European Patent Application 0,304,617 to Kao Corporation discloses a perforated film wherein the orifice is in the sidewall of the three dimensional structure of the die, thereby providing a hole in the sidewall of the protruded film.

Three dimensional films containing perforations have also been formed by embossing an already perforated film to form pockets, corrugations and the like, as in U.S. Pat. No. 4,798,604 to Carter. Various means have been used to reduce the common shiny film appearance of plastic film to give it a matte finish and to make it look and feel more fabric like. Examples of such means are: microembossing; molding in microbubbles or micronubbles, as in U.S. Pat. No. 4,327,730 to Sorensen and U.S. Pat. No. 4,463,045 to Ahr et al; chemical means, e.g., by caustic or solvent etching; and by abrading the surface of the film.

Perforate films of the prior art, both flat and three dimensional, as well as many flat or almost flat nonwoven fabrics, suffer from the serious drawback that the specific part of the product that touches the body is that of a significant surface area or enclosing volume of plastic that is occlusive, uncomfortable, hot and non fluid absorbing. The occlusiveness of perforated plastic films is compounded by contact with the body of a plastic surface that is relatively unrelieved by perforations. The problem of unrelieved plastic contact is solved only to a slight degree by embossed perforate films. Only appearance and tactile perception are appreciably changed by creating microembossed matte finishes, since the micro surface does not solve the macro difficulty of unrelieved close adhering discomfort and poor fluid transfer through the non perforate areas. Even when films with three dimensional holes, e.g., funnel-like, are turned upside down, to present the exit orifice side to the skin, the results are unsatisfactory. The exit orifices and their defining film perimeters are easily crushed on contacting the body to fold the film perimeters downward and inward, thereby presenting uncomfortable plastic surfaces to the body and, furthermore, decreasing and possibly closing the exit orifices to fluid. In addition, the possible absorbency advantage of having a capillary driving force of fluid from larger to smaller capillary sizes, by having a larger entry orifice than the exit orifice, is removed by now having the size of the orifice in contact with the body being smaller than the entry orifices.

SUMMARY OF THE INVENTION

It is accordingly an object of this invention to provide an absorbent product that has a permeable cover, of a microperforated fibrillated thermoplastic film, that is in intimate, but nonoccluding, contact with the body, while providing comfort, resilience and immediate fluid-acceptance and efficient transfer of fluid laterally and to the absorbent body below.

It is a further object of this invention to provide an absorbent product having a microperforated fibrillated thermoplastic film cover that has elevated perforate regions comprised of a plurality of microholes defined by a network of fiberlike elements, the perforate regions being in intimate contact with fluids emanating from the body and being capable of efficiently wicking fluid away from the body and into the absorbent product.

It is yet a further object of this invention to provide means for attaching such a film to the absorbent product so that benefits such as nonoccluding and immediate fluid-accepting contact are attained.

In accordance with one aspect of the present invention, there is provided an absorbent product used to absorb body fluids, such as diapers, incontinence products, surgical dressings, underpads and the like. comprised of a permeable cover, an impermeable barrier and an absorbent body therebetween. The permeable cover comprises a microperforated fibrillated stretchable thermoplastic film having perforate regions and nonperforate regions, the perforate regions having at least a plurality of microholes defined by a network of fiberlike elements. The perforate region may also comprise holes that are larger than the microholes. The perforate regions are further distinguished by being, at least in part, at elevations that are higher than the nonperforate regions, with reference to the absorbent product; thereby having the perforate regions in intimate contact and the nonperforate regions not in contact with the body. Additionally, the superstructure of the permeable cover can be roughly described as a pattern of perforate hill regions and nonperforate valley regions, the hills being comprised of fiberlike elements separated by microapertures of different hydraulic diameters and the fiberlike elements being of different lengths.

Several advantages are realized from having the perforate regions higher, than the nonperforate regions, with respect to the plane of the film and with respect to the absorbent product; and where the perforate and nonperforate regions are immediately adjacent to each other. One advantage, from having the network of fibrillar elements and the plurality of microholes that define the perforate regions be higher than the film portion that defines the nonperforate regions, is that the network of fibrillar elements and the plurality of microholes are in limited point contact with the body, and the nonperforate regions are not in contact with the body; thereby providing enhanced air circulation and a soft, resilient, cool and comfortable product. Thus, there is none of the hot, clinging plastic feel of the perforated products of the prior art including those products whose perforations are within the plane of the film or even those whose perforations are three dimensional.

Another advantage that has been surprisingly found is that having an elevated network of fibrillar elements and microholes does not compromise the absorbency characteristics of the product. In fact, the fibrillar elements actively wick fluid into the absorbent product; when it might be expected that the network, being above the surface of the absorbent body, would provide an air space therebetween that might prevent fluid from rapidly reaching the absorbent body. It is further surprising to find that the perforated cover on the absorbent product of this invention, having a modest open area of about 1% to about 15%, permits active wicking of the fluid into the absorbent product. Thus, the result of the active wicking of the elevated network of fibrillar elements and microholes is such that the absorbency characteristics of the product of this invention, are at the very least equal to and even improved compared to a product made with the same microperforated film wherein the fibrillar elements are depressed and in contact with the absorbent body. It would appear, not be bound by such explanation, that the network of fibrillar elements and plurality of microholes provides immediate contact with the body fluid, as it emanates from the body, to accept and transfer the fluid by wicking the fluid both laterally and downward to the absorbent body below. Additionally, the pattern of perforate hill regions and nonperforate valley regions of the cover of this invention serve to channel fluid within the confines of the cover until such time as the fluid is absorbed through the cover, thereby preventing side leakage.

The three dimensional hill and valley superstructure of the cover provides an inherent resilience and springiness. Superimposed on this is the inherent resilience and springiness of the local structure of the elevated fiberlike elements of the perforate region. The hill and valley superstructure and the fiberlike elements combine to provide resilience to the absorbent product covered with such a material. This combination of hill and valley superstructure and fiberlike elements local structure also permit the cover to neatly drape the product such that the transition, from high to low areas of the product and from flat to and around curved surfaces, is effected in a smooth, esthetically pleasing fashion, with no wrinkling or creasing.

Some benefits, resulting from the springy, resilience of the cover of this invention, are to provide products that have a cushiony, soft feeling during wear. Additionally, if the product is packaged in a folded configuration, e.g., bifold or trifold, the product will tend to spring open ready for use. Also the resilience that the cover lends to the product does not permit the product to be unresistingly hard-folded to a sharp crease. Minimization of such creasing also reduces the destabilizing cracking or breaking of the absorbent core, and reduces the liquid runoff along such breaks and cracks that may result in side leakage. In addition the appearance of the product will be esthetically more pleasing due to minimization of such creases.

DETAILED DESCRIPTION OF THE INVENTION

The present invention is directed to absorbent products, such as a sanitary napkin, that is comprised of a permeable cover, an impermeable barrier and an absorbent body therebetween. Each of these components and their alternative embodiments will be described in detail. Also to be described in detail are the embodied designs and constructions of the napkin, and the interactions between and among the components.

The cover material for the absorbent products of this invention is preferably made from microperforated fibrillated stretchable thermoplastic film materials. Such materials and their method for making is described in "Textilelike Apertured Plastic Films", Canadian Patent Application 2,130,176 to Turi et al, and commonly assigned, herein incorporated in its entirety by reference. The method of making such films is by directing controlled fluid forces, wherein water is an example of such fluid, against one surface of a relatively thin, stretchable plastic film while the film is supported on its other surface by a backing member. Examples of such fluid forces are those of columnar streams of liquid, directed from small diameter orifices, against the supported film. Backing members suitable for use in the practice of producing the cover of the present invention comprise localized support regions for supporting the film; recessed zones into which the film may be deformed by the application of the fluid forces thereto; and means for removing the applied fluid from the backing member. The controlled fluid forces against the film when supported on such backing members results in deforming the film into the recessed zones and at the same time rupturing it. The resulting microperforated fibrillated film materials comprise a plurality of microholes defined by a network of fiberlike elements or microstrips, also called fibrils, of drawn plastic material, the microholes being for the most part of irregular shape, i.e., not having a clearly identifiable geometric configuration such as square, circular or oval. The microholes may be provided in a discontinuous pattern of distinct clusters. The pattern may be either random or regular. However, the microholes in a random or regular pattern of clusters may be randomly distributed therein. Furthermore the microholes are of nonuniform size and have small equivalent hydraulic diameters.

The fiberlike elements cooperate with the microholes to give the plastic film a visual appearance and functional attributes of textiles, such as spunbond nonwovens or nonwovens made from airlaid staple length fibers; where examples of such attributes include and relate to tactile benefits such as improved resilience, comfort, softness, drapeability, coolness and to absorbency characteristics such as good wicking and reduced wetback that result in a clean and dry product surface and leakage protection. The fiberlike elements having lengths ranging from about 0.005 inch (0.013 cm) to about 0.05 inch (0.127 cm);. widths ranging from about 0.001 inch (0.003 cm) to about. 0.035 inch (0.089 cm); and thicknesses ranging from about 0.00025 inch (0.0006 cm) to about 0.002 inch (0.005 cm). The films may have open areas, provided by the microholes, ranging from about 1% to 15% of the total surface area of the film. The films may also have secondary openings, where the area of each secondary opening is larger than any of the microholes.

The cover material for the absorbent products of this invention may also comprise larger apertures and greater open area than described above, so that viscous fluids such as menses may flow more readily through the film. Such properties are imparted to the film by subjecting the film to fluid forces in the form of columnar streams from at least one set of orifices of larger size than those of the previously cited Canadian Application 2,130,176; or more than one set of apertures can be created in the film by subjecting the film to fluid in the form of columnar streams from at least two sets of orifices, one set being of relatively large orifice size and emitting fluid of low pressure, in comparison with another set of orifices of small orifice size and emitting fluid of higher pressure, thereby creating at least two different sizes of apertures. Such materials and their method of making is described in the Patent Application, commonly assigned and concurrently filed herewith, entitled, "Method of Forming Improved Apertured Films, Resultant Apertured Films, and Absorbent Products Incorporating Resultant Apertured Films", herein incorporated in its entirety by reference. Additionally, the cover material for the absorbent products of this invention may be made to have improved fluid acceptance and distribution properties by treating with a corona discharge the male side, i.e., the smooth protruding embossed side, of a preembossed film. The male side is the side placed against the surface of the backing member during the microperforating process and is also the side of the microperforated film that is preferably placed against the absorbent body of the absorbent product. It was further found that surfactant, applied to the female side of the film after microperforating and rolling up undried film, will also transfer to the male side of the film, thereby further enhancing the fluid acceptance and distribution properties of the film. Such materials and the method for making is described in another commonly assigned Patent Application, also concurrently filed herewith, entitled, "Apertured Film Having Improved Fluid Distribution Properties, Method of Forming Same, and Absorbent Products Incorporating Same", herein incorporated in its entirety by reference.

The films may be made from any of a variety of stretchable thermoplastic films. Preferred stretchable thermoplastic film materials may be chosen from many types of polymeric films, including but not limited to, polyethylene, preferably, low and medium density polyethylenes, polypropylene, blends of polyethylene and ethylene vinyl acetate and blends of polypropylene and ethylene vinyl acetate. Such films may be made wettable, to varying degrees, by treating the film with a surfactant, by exposure to corona discharge, by grafting the film with wettable reactants, by caustic etching of films such as polyester, by incorporating wettable polymers such as polypropylene oxide and polyvinyl alcohol within the polymeric formulation used to make the film, and the like, and combinations thereof.

Films made from polyethylene, preferably in entire range of low and medium densities are especially preferred for their characteristics of being capable of being deformed into the recessed zones of the forming surface and at the same time being ruptured to give the fiberlike elements that define the microholes and secondary openings. Thin films are preferred over overly thick films since less fluid force is required to deform and rupture the film. Embossed films are particularly preferred, since they provide facile deforming and rupture of the film. An example of such film is 1.0 mil thick embossed film comprising 50% by weight of linear low density polyethylene and 50% by weight of low density polyethylene, such a film being obtained from Exxon Corporation under the designation EMB-631, the film being further characterized as being microembossed to contain thick and thin areas. Another example of such a film, also microembossed, is comprised of a blend of low and linear low density polyethylenes obtained from Edison Plastics, Edison, N.J. is designated as MFST 141.

Suitable microperforated fibrillated stretchable thermoplastic films generally comprise nonperforate regions and perforate regions, the perforate regions having a plurality of microholes and possibly larger apertures, defined by network of fiberlike elements. The perforate regions of microholes, larger apertures and fiberlike elements are at a lower level than are the nonperforate regions, with respect to the body facing side of the absorbent product. Embodiments of such films include different designs and configurations of perforate and nonperforate regions. Examples of such embodiments, not to be restrictive to same, are: 1. A film comprised of a series of parallel ridges and a series of valleys between the series of ridges, each of the ridges being formed by a pair of generally vertically oriented sidewalls which meet on the upper surface of the film, the valleys comprising a plurality of microholes defined by the network of fiberlike elements. 2. A film comprised of nonperforate regions and perforate regions, the non perforate regions being comprised of a plurality of generally upwardly oriented conelike structures, the perforate regions being comprised of a series of valleys between the conelike structures, the valleys comprising a plurality of microholes defined by a network of fiberlike elements. 3. A film comprising nonperforate regions and perforate regions, the perforate regions being comprised of a plurality of microholes, the microholes being defined by a network of fiberlike elements and being arranged in a plurality of groups of microholes. Needless to say if one covers an absorbent product with such a microperforated fibrillated stretchable thermoplastic film, unperturbed in the method of attachment, the original relative elevational relationships of perforate and nonperforate regions will be retained.

It is considered an important feature of the present invention that the perforate regions of the permeable cover reverse their elevational relationships, with the perforate regions being at a higher elevation than that of the nonperforate regions. Thus, the perforate regions are higher and further away from the absorbent body, thereby being in contact with the body of the user, than are the nonperforate regions. The method used for effecting the reversal of the elevational relationships is not, per se, critical to the invention, provided of course that the resultant product possesses a fluid permeable cover having perforate regions being at a higher elevation than that of the nonperforate regions. One suitable method for achieving the reversal of the elevational relationship of perforate and nonperforate regions is by tensioning the perforate film. A second suitable method for achieving such reversal is by preferentially adhering the nonperforate regions of the film to the absorbent body. A third suitable method for achieving such reversal is by both tensioning the perforate film and preferentially adhering the nonperforate regions of the film to the absorbent body. A fourth suitable method for achieving such reversal is by attaching the perforate cover material as it is made with the face downward toward the absorbent body of the absorbent product so that the already downwardly facing nonperforate regions are already against the absorbent body and the perforate regions at an elevation higher and away from the absorbent body. A fifth suitable method of achieving such reversal of perforate and nonperforate regions of the perforate cover, as it is being made, is by blowing air from the side of the cover that has the perforate regions at a lower level so as to invert the perforate regions to higher elevations. Of course, care must be taken, in the last two described methods, not to reverse the relative elevations of perforate and nonperforate regions by the methods of tensioning and attachment used to fix the cover to the absorbent body and to the impermeable barrier. Other methods of achieving such reversal will be readily apparent to those of ordinary skill in the art.

It has unexpectedly been found that merely attaching the microperforated film in a tensioned condition, with or without adhering it to the absorbent body of the absorbent product, the perforate regions and the nonperforate regions reverse their elevational relationships, the perforate regions being higher and further away from the absorbent body than are the nonperforate regions. Unexpected are both the fact that the elevational relationship of the film's perforate and nonperforate regions can be reversed and that it can be facilely effected by the application of tension. The tension may be applied to the microperforated film in the machine direction, the cross direction or biaxially, in the machine and cross directions. The tension required to cause this reversal is modest, such tension being at least about 2 grams/inch, as measured by the method given below. Of course, the tension required to cause reversal will depend on such factors as the material from which the film is made, its thickness and stretch characteristics, its particular perforate and nonperforate pattern and the dimensions of the fibrils and perforations that make up the perforate regions as well as the dimensions and configuration of the nonperforate regions.

Tensioning Test Method: A sample of a perforated film is laid over a pulp pad that is attached to a horizontal sled on an Instron 1122, the film samples being oriented so that variable tension may be applied to the film in either the machine or cross direction. If the effect of tension is to be measured in the cross section, one cross direction edge of the sample, the sample being at least six inches wide in the machine direction, is anchored to the sled. The free, unattached cross direction edge is grasped in a six inch jaw of the Instron and pulled in the cross direction, using a tension that can be measured in the direction away from and parallel to the attached cross direction edge, at a crosshead speed of one inch/minute; using a chart speed of 10 inches/minute.

If the effect of tension is to be measured in the machine direction, one machine direction edge of the sample, the sample being at least six inches wide in the cross direction, is anchored to the sled. The free, unattached machine direction edge is grasped in a six inch jaw of the Instron and pulled in the machine direction, using a tension that can be measured in the direction away from and parallel to the attached machine direction edge, at a crosshead speed of one inch/minute, using a chart speed of 10 inches/minute.

If the effect of tension is to be measured biaxially, in both the machine and cross directions, the film is anchored to the sled on both a cross direction edge and an adjacent machine direction edge. Then, a 192 gram weight is hung, from the remaining free machine direction edge, for example, and the free unattached cross direction edge is grasped in a six inch jaw of the Instron and pulled in the cross direction, using a tension that can be measured in the direction away from and parallel to the attached cross direction edge, at a crosshead speed of one inch/minute, using a chart speed of 10 inches/ minute.

The response of the perforated film is viewed and recorded directly, as tension is applied to the film, using for example a video camera equipped with a macro lens to view single perforate and nonperforate areas and thereby determine at what tension reversal is occurring.

It has also been found that such reversal of the elevation of the perforate regions can be effected even without tension by preferentially adhering the nonperforate regions of the film to the absorbent body. This is easily done with adhesive, since on coating the film, more adhesive mass will accumulate on the greater exposed and thereby more accessible film area of the nonperforate regions. Solvent-based or hotmelt adhesives may be used, with the hotmelt adhesives being preferred for more precise coating of one side of the film and for ecological reasons. Solvent coating may be done, for example, by gravure or transfer coating. Hotmelt adhesives may be applied, for example, by spray or knife coating.

Other methods of adhering the film may be by thermal bonding of the film itself or by placing thermally bondable fibers or powders between the film and the absorbent body and then applying heat. Ultrasonic or radiofrequency bonding may also be used. Mechanical boding such as with hot needles or by needlepunching may also be used. The particular method of bonding used to adhere the cover to the absorbent product is not critical, provided of course that it results in the perforate regions being maintained at a higher elevation than the adjacent nonperforate regions. Of course, care must be taken not to adhere the film so assiduously so that all the material, both perforate and nonperforate, is matted and plastered down. The resultant bonded products will have, by virtue of the flexible fibrillar elements, more flexible material in the perforate region than in the nonperforate region. Therefore, any nonbonded material, whether perforate or nonperforate, will move by paths of least resistance either toward the absorbent body or away from it. The perforate material will more likely move in an upward direction, due to its greater flexibility and having a greater span of material.

The absorbent body may be comprised either of simple or complex absorbent core structures that accept, transfer, distribute, store and retain fluid as well as prevent fluid from exiting the absorbent product. The absorbent core may be a simple absorbent such as woodpulp, which may contain stabilizing components such as synthetic fibers that are used as such to form a bridging matrix; or by being thermobondable, are fused to themselves and to the woodpulp to form a dimension stabilizing structure. The synthetic fibers may be either hydrophilic, such as rayon, or hydrophobic such as polypropylene and polyester. The synthetic fibers may be made more wettable by treatment with a wetting agent such as a surfactant, by caustic etching of fibers such as polyester, by incorporating wettable polymers such as polyethylene oxide or polyvinyl alcohol within the fiber polymer formulation, by grafting the fiber surface with wettable reactants and by exposing the fiber to corona discharge. The peripheral profile of synthetic fibers may be of any shape. The synthetic fibers may also contain grooves, channels or bores; and may be pitted or perforated. The absorbent core may also contain auxiliary absorbents such as rayon or cotton fibers, sphagnum moss and superabsorbent fibers or particles.

Absorbents such as sphagnum moss, in board or in compressed layer form, may function additionally as compression resisting or deformation resisting structures or to help maintain a flat or raised product profile. Absorbents in board form may be made flexible and conforming by tenderizing by means of passing the board through a corrugating or embossing process. The woodpulp itself may also be at least in part comprised of any of wet crosslinked, dry crosslinked, chemically stiffened or curly fibers. The synthetic fibers and auxiliary absorbents may be present homogeneously throughout the absorbent core, in discrete layers or in continuous or discontinuous concentration gradients. The absorbent core may also contain foam in the form of layers or particles, the foam being either hydrophobic or hydrophilic, depending on its place and function in the product, e.g., absorbing, cushioning, deformation resisting and compression resisting. The absorbent core may be uncompressed, compressed, or otherwise densified, at least in part. Compression and densification may be homogeneous throughout the absorbent core or in discrete layers or in continuous or discontinuous gradients of density.

The absorbent body may contain, in addition to the absorbent core, a transfer layer, which is a low density fluid accepting and releasing layer, usually located between the absorbent core and the permeable cover. The transfer layer may be comprised of relatively less hydrophilic materials and structures, than is contained in the absorbent core, such as webs of meltblown polypropylene or polyester fibers. Such webs may also contain woodpulp entrained within. Transfer layers may also be comprised of low density, highloft nonwoven webs comprised of woodpulp and synthetic fibers such as polyethylene, polypropylene, polyester, polyacrylonitrile and polyamide. Such highloft webs may be bonded with chemical binders or by thermal means such as through-air bonding.

The impermeable barrier can be of any flexible material that prevents the transfer through it of fluid but does not necessarily prevent the passages of gases. Commonly used materials are polyethylene or polypropylene films. Other materials that may be used as impermeable barriers may be chosen from films of polyesters, polyamides, ethylene vinyl acetate, polyvinyl chloride, polyvinylidene chloride, cellophane, nitrocellulose and cellulose acetate. Coextruded and laminated combinations of the foregoing, wherein such combinations are permitted by the chemical and physical properties of the film, may be used. Fluid impermeable nonreticulated foams and repellent treated papers may also be used. Films that are fluid barriers, but permit gases to transpire, i.e., "breathable films", may be used. These may be chosen from polyurethane films and from microporous films, where microporosity is created by ionizing radiation or by leaching out of soluble inclusions using aqueous or nonaqueous solvents.

The permeable cover of the absorbent product of this invention may cover any part or all of the upper surface, that is the body facing surface, of the absorbent body. It may alternatively wrap the absorbent body partly or entirely around. Part wrapping of the absorbent body is exemplified by the permeable cover covering the top of and the sides of the absorbent body. The impermeable barrier may cover at least the entire bottom surface, that is the garment facing surface, of the absorbent body. It may also wrap around to cover the sides of the absorbent body and even part of the body facing surface of the absorbent body. The permeable cover may be fixed or otherwise adhered to the surface of the absorbent body overall or in discrete zones of attachment. Depending on the degree of coverage and wrapping of the absorbent body by the permeable cover, the permeable cover may be adhered to itself for example in an overlapping configuration at the bottom of the absorbent body. It may be adhered to the impermeable barrier in an overlapping configuration for example parallel to the sides of the napkin or parallel to the bottom of the napkin or in a flange seal extending from the sides of the napkin. When the cover and impermeable barrier are adhered to each other in a flange seal, the permeable cover may additionally be wrapped around the flange seal about the impermeable barrier; or the impermeable barrier may additionally be wrapped around the flange seal about the permeable cover. The napkin may be provided with a means for attaching it to the undergarment such as adhesive, protected by release paper until use, or by a hook and loop assembly.

It should be noted that the absorbent products of this invention have perforate covers of a microperforated fibrillated stretchable film which has perforate hill regions and nonperforate valley regions covering at least a portion of the absorbent product. For esthetic and functional reasons, at least part of the absorbent product may have portions covered by microperforated film wherein the perforate regions are at a higher or equivalent elevation compared to the nonperforate regions. These portions of the absorbent product may include part or all of each of the napkin's body facing surface, its sides, part of its garment facing surface and auxiliary components such as wings, tabs and cuffs, that will be described below. It should be noted, that for esthetic and functional reasons, part of the absorbent product may also have portions of its surface covered by microperforated film; wherein the perforate regions are at lower elevations compared to the nonperforate regions. It is also possible to have part of the absorbent product of this invention covered with perforated film that is different from the microperforated fibrillated stretchable film of this invention.

When tensioning is used to effect the transition where the permeable cover has perforate regions at a higher elevation, and means of adhering are not used to effect such transition, the permeable cover needs to be fixed at least at or outward of the region wherein the transition is desired. Tensioning can be done in the machine direction, cross machine direction or both. It may be effected, in the process and machinery that make the product, by applying tension to the permeable cover material before it is attached to the product. Tensioning may also be effected when laying the permeable cover onto the product: in draping the high to low thickness areas as in a product having a raised center and thinner lateral or transverse sides; in the transition from higher portions of the product to the edges of the product where cover is sealed to barrier film in for example a flange seal; and in the transition from relatively raised portions such as a thick center region and thick lateral side regions to depressed regions such as deeply embossed channels. Tensioning may be done by any of several means wherein the permeable cover is tensioned on attaching it to the product, as follows: adhering the cover to itself, for example in overlap; adhering the cover to the absorbent body; adhering the cover to the impermeable barrier film in overlap or in a flange seal. Tensioning can be done in use by the user as follows. A napkin may be made by attaching the permeable cover to the absorbent body, while the absorbent body is concavedly flexed from one lateral side to the other or concavedly flexed from one transverse side to the other. When the napkin is applied to a user's undergarment, contact imposed on the product by the user's body causes a lateral and longitudinal flattening of the napkin that will in turn cause the perforate regions of the permeable cover to elevate.

The absorbent product of this invention may also be provided with channels, to stabilize the structure and to provide barrier structures to prevent leakage to the lateral or transverse edges of the product, depending on the design, depth, densification, materials of construction and placement of the channels, with respect to that of the rest of the product.

The absorbent products of this invention may also comprise auxiliary components that may add to the functional, comfort and esthetic properties of the products. The products may include any or all of wings, tabs and cuffs. The wings, tabs and cuffs may be attached to be extensions of the sanitary napkin of its body facing side, napkin sides or garment facing side. The wings, tabs or cuffs may be comprised of materials that are different from those of the napkin, or may be comprised of materials of which the napkin is made, or of combinations of the different materials and the materials of which the napkin is made. When the wings, tabs or cuffs are made of the materials of which the napkin is made, the materials may be attached to the napkin or be formed of extensions of the napkin's materials. Examples of constructions of wings, tabs or cuffs are: where the permeable cover material and the impermeable barrier material are attached to themselves, or to each other, along the periphery of the wing, tab or cuff structure, in discrete areas, or over their entire area of contact. The wings, tabs and cuffs may have laminated, between the cover and barrier materials extensions of part or all of the absorbent body, for example of one or both of the transfer layer and a portion of the absorbent core. The wings and tabs may be provided with adhesive, protected with release paper, for attachment to the undergarment. The cuffs may also comprise additional materials to make them thick and cushioning and may also comprise elastic materials to gather or curve the cuffs or the napkin or both.

The design and structure of the absorbent products of this invention, with special attention to the permeable cover thereof, will now be described in greater detail with reference to the cited figures, with identical components of the figures being given the same identifying numbers.

Figure 1:
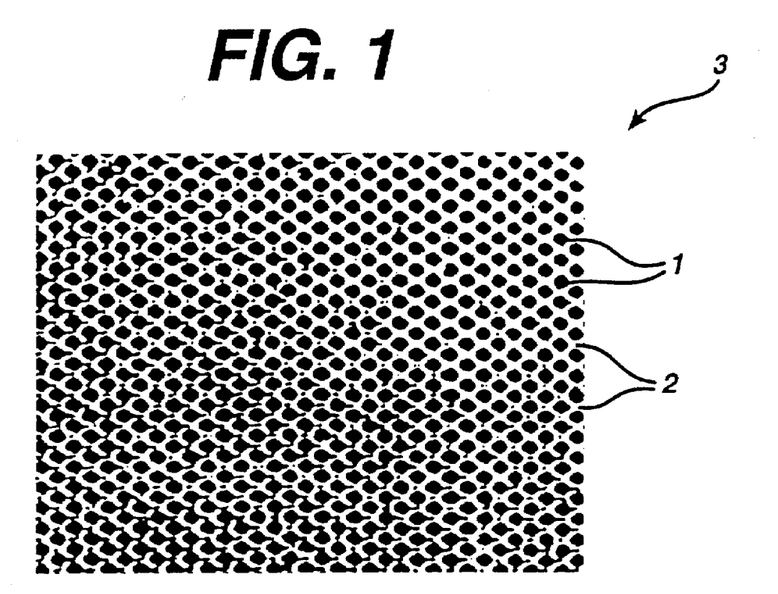
FIG. 1 is a plan view of a perforated film of the prior art.

FIG. 1 shows a plan view of perforated film 3 of the prior art, the film being comprised of perforate areas 1 and non perforate areas 2. Such a perforated film is made, as is described in U.S. Pat Nos. 4,690,679 and 4,806,411 to Mattingly et al and in U.S. Pat. No. 4,859,519 to Cabe et al, by embossing a film, to thin the film in the depressed embossed areas, and then stretching the film until the thinned embossed areas are burst open to create perforations. The film of these inventions may be doubly embossed, one of which may be microembossing to give a soft, comformable film with a matte finish.

Figure 2:
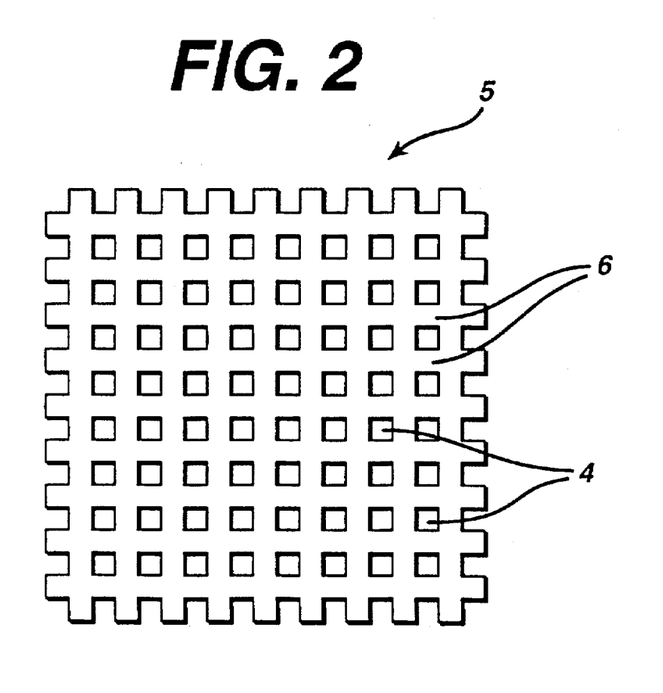
FIG. 2 is a plan view of another perforated film of the prior art.

FIG. 2 shows a plan view of another perforated film 5 of the prior art having perforate areas 4 and nonperforate areas 6. This type of perforated film is made, as described in U.S. Pat. No. 3,504,148 to Zimmerli, by applying pressure to a plasticized thermoplastic film on a perforated support or molding element until the film ruptures.

Figure 3:
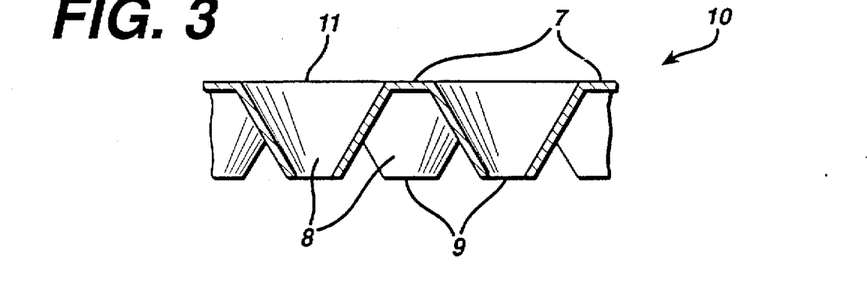
FIG. 3 is a cross sectional view of yet another perforated film of the prior art.

FIG. 3 shows a perspective view of yet another perforated film 10 of the prior art, as is described in U.S. Pat. No. 3,929,135 to Thompson et al and in U.S. Pat. No. 4,324,246 to Mullane, having three dimensional perforate areas 8 and flat nonperforate areas 7, the perforations being tapered capillaries having base openings 11 that are larger than apex openings 9. This type of perforated film is made, analogously to a previously noted perforated film, by drawing hot air that impacts film that is supported on a perforated drum to which a vacuum is applied. However, here the perforations of the drum are three dimensional, e.g., a truncated cone, so that the film is drawn down into the truncated cone perforations of the perforated drum to the point that the film finally is burst at the apex of the cone, thereby yielding a flat film that has pending from it funnel like projections each having a perforation at its base.

It should be noted that in all of these perforated films, which are considered representative of the prior art, both the perforate and nonperforate areas, the nonperforate areas being also known as "land areas", on the body facing side of products covered with such films, are essentially coplanar. Therefore, the use of these films the body facing surface of an absorbent product results in a product where both perforate and nonperforate areas are equally likely to contact the body. To be additionally noted, is that the body contacting nonperforate areas of the prior art perforated films are essentially devoid of perforations. Therefore, the contact with the body of these nonperforate areas is occlusive. In contrast, the nonperforate areas of the cover on the absorbent product of this invention does not contact the body and therefore cannot be occlusive.

Figure 4:
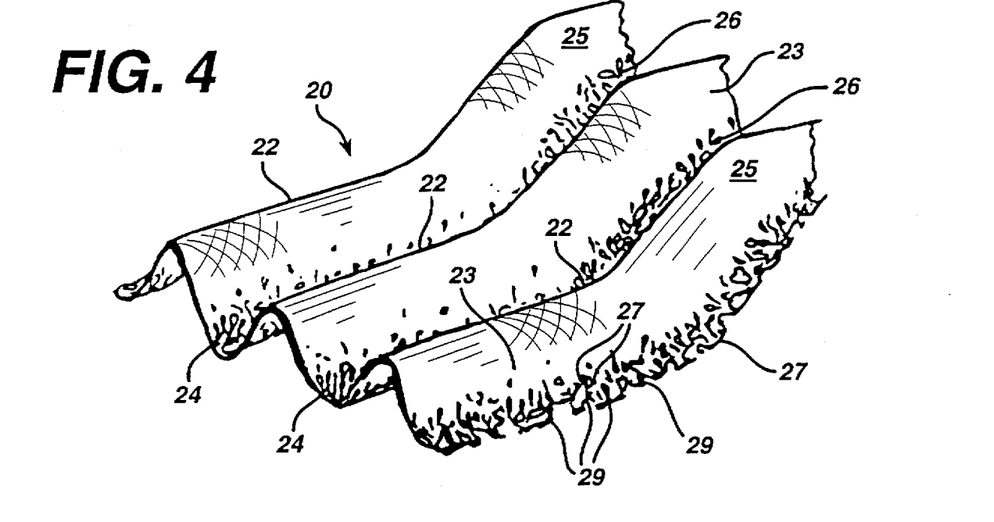
FIG. 4 is a perspective view of one embodiment of a perforated film used in this invention before it is attached to the absorbent products of this invention.

FIG. 4 shows a perspective view of an embodiment of the perforated film 20 used to make the absorbent products of this invention before it is attached to the absorbent products. The perforated film, unperturbed by a mode of attachment, is distinguished by being comprised of a series of parallel ridges 22, that are essentially nonperforate regions 25, and a series of valleys 26 between the series of nonperforate ridges 22, each of the ridges 22 being formed by a pair of generally vertically oriented sidewalls 23, which meet on the upper side of the film 20, the valleys being perforate regions 24 comprising a plurality of microholes 29 defined by a network of fiberlike elements 27. Thus, the unperturbed and unattached perforated film 20 has perforate regions 24 comprised of microholes 29 and fiberlike elements 27 that are at a lower level than are the nonperforate regions 25. All other embodiments of such perforated films, albeit with different designs and configurations of perforate and nonperforate regions, will have the perforate regions at levels that are lower than those of the nonperforate regions. And therefore, a product covered with such a perforated film, but unperturbed by the method of attachment, will retain the same relative elevational relationships of the perforate and nonperforate regions as that of the unperturbed perforated film.

Figure 5:
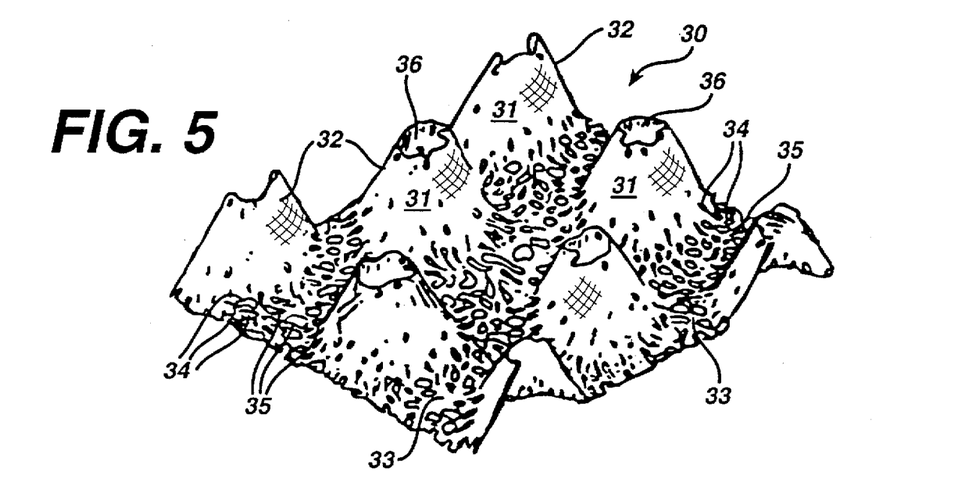
FIG. 5 is a perspective view of another embodiment of a perforated film used in this invention before it is attached to the absorbent products of this invention.

FIG. 5 shows a perspective view of another embodiment of the perforated film used to make the absorbent products of this invention before it is attached to the absorbent products. Perforated film 30 comprises a plurality of generally vertically extending conelike structures 31 whose sloping sidewalls 32 define valleys 33 therebetween. Valleys 33 and adjacent portions of sidewalls 32 of conelike structures 31 comprise a large plurality of microholes 34 defined by a network of very fine fiberlike elements 35. Conelike structures 31 also comprise secondary openings 36 whose areas are substantially larger than the areas of microholes 34.

Figure 6:
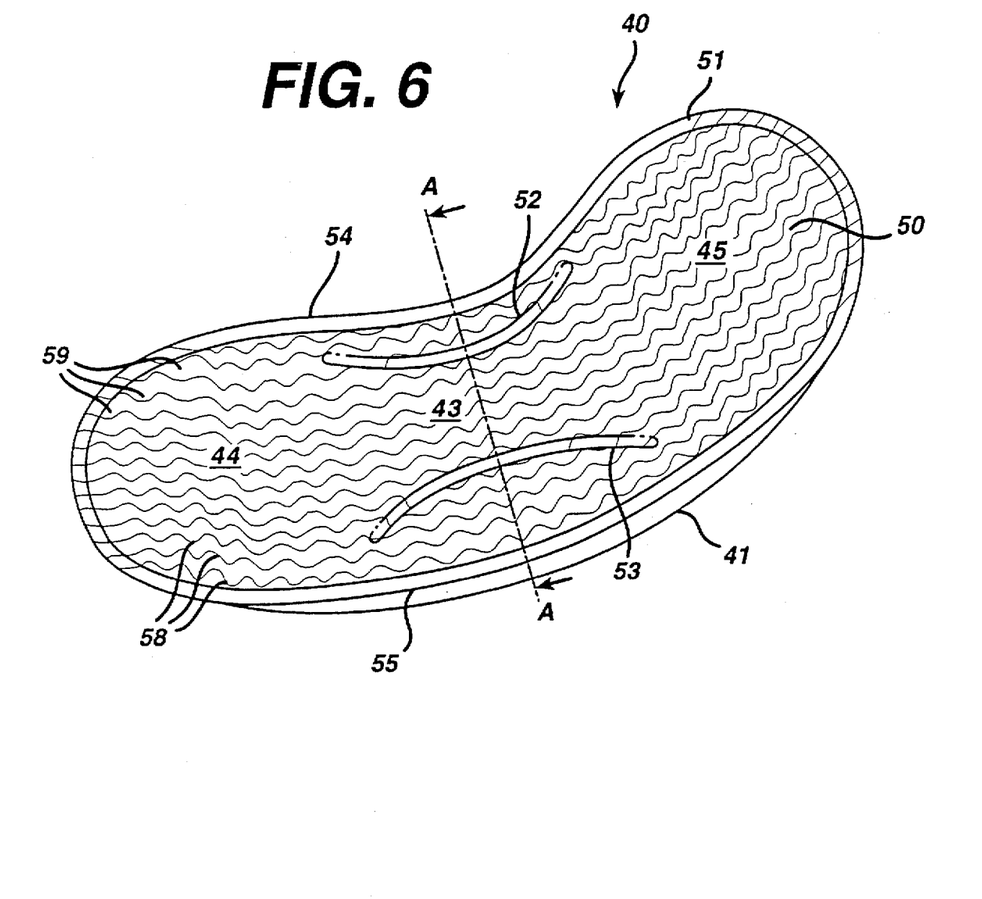
FIG. 6 is a perspective view of a sanitary napkin in accordance with this invention.
Figure 7:
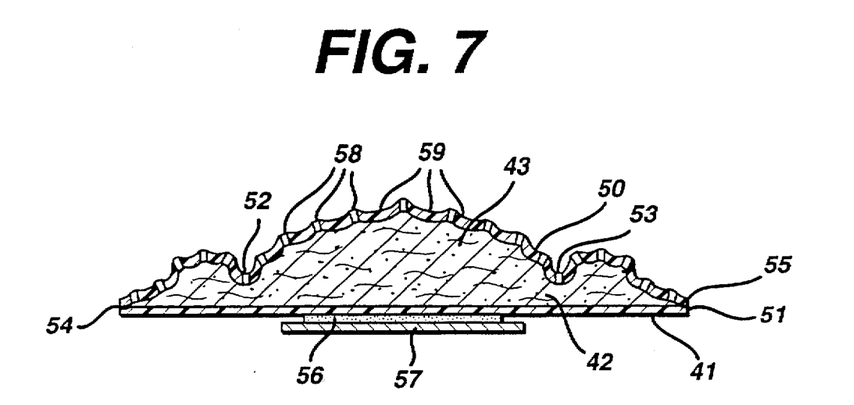
FIG. 7 is a cross-section of the sanitary napkin shown in FIG. 6.

FIG. 6 shows a perspective view of an absorbent product of this invention, here a sanitary napkin 40 covered by a perforated film cover 50, a barrier film backsheet 41 and an absorbent body 42 therebetween. FIG. 7 shows a cross-section of sanitary napkin 40 taken along line A—A of FIG. 6. The absorbent body 42 is comprised of an absorbent, for example woodpulp, the absorbent body 42 having more absorbent, thereby being thicker in approximately the central portion 43, i.e., approximately the central third, then becoming thinner by tapering down toward the transverse ends 44, 45 of napkin 40. Napkin 40 is distinguished by having perforated film cover 50 sealed along its entire periphery 51 to barrier film backsheet 41. Napkin 40 is further distinguished by having a pair of deeply embossed concavedly curving channels 52, 53, toward and adjacent each of two lateral sides 54, 55 respectively, along and outward of the central portion 43 of napkin 40, the deeply embossed channels 52, 53 being a highly densified region containing the perforated film cover 50 and a significant depth of the absorbent comprising absorbent body 42. The thickness of the absorbent body 42 in central portion 43 between the pair of channels 52, 53 is at least equal to or greater than the thickness of central portion 43 between pair of channels 52, 53 and lateral sides 54, 55. Napkin 40 also comprises a positioning adhesive 56, on the garment side of barrier film backsheet 41, for attaching napkin 40 to an undergarment, positioning adhesive 56 being protected until use with a release paper 57. Absorbent body 42 may optionally contain as distinct layers, gradients, or as homogeneous dispersions, any or all of absorbents such as tissue, sphagnum moss and superabsorbent.

With continued reference to FIG. 6 and especially to FIG. 7, perforated cover 50 is further described, and differentiated from the unperturbed and unattached cover. Perforated cover 50, now having been appropriately adhered or tensioned, or adhered and tensioned, to absorbent body 42, exhibits perforate regions 58, being elevated with respect to nonperforate regions 59, the perforate regions 58 being further described and illustrated, but not restricted to the embodiments shown in FIGS. 4 and 5, as being comprised of a plurality of microholes, defined by a network of fiberlike elements; the fiberlike elements of cover 50, when attached to napkin 40, being raised above the surface of absorbent body 42 and at an elevation that is greater than that of nonperforate regions 59. There are areas of napkin 40 that require more tensioning of perforate cover 50 than others. An example of such an area is raised central portion 43. The tensioning required to neatly cover and drape this area at times results in a flattening of permeable cover 50 sufficient to reduce the elevational difference between perforate regions 58 and nonperforate regions 59. However, an elevational difference is still maintained such that perforate regions 58 are still higher than nonperforate regions 59.

Figure 8:
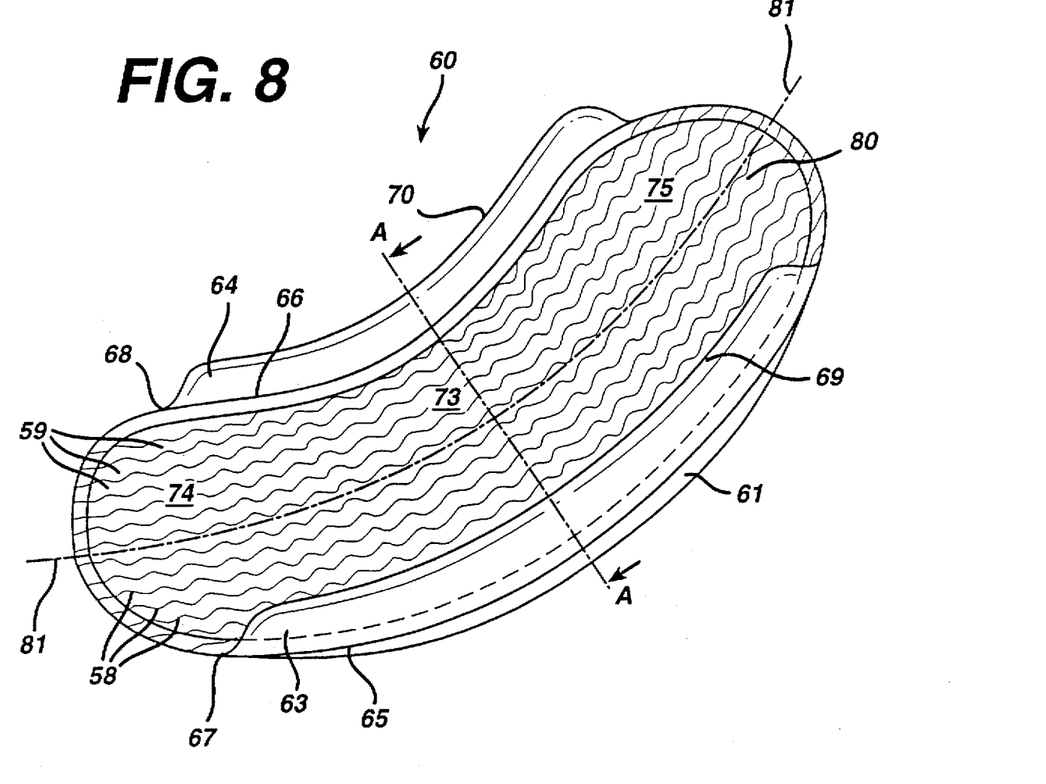
FIG. 8 is a perspective view of another sanitary napkin in accordance with this invention.
Figure 9:
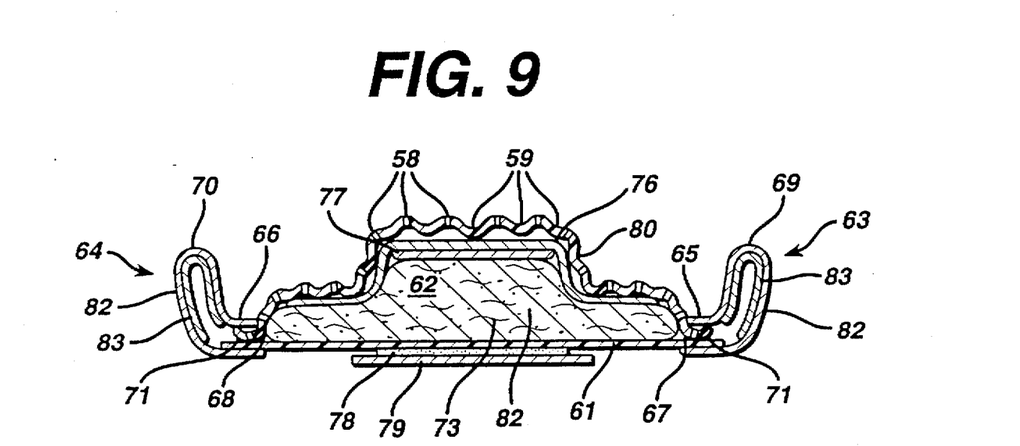
FIG. 9 is a cross-section of the napkin shown in FIG. 8.

FIG. 8 shows a perspective view of an absorbent product of this invention, a sanitary napkin 60 covered by a perforated film cover 80, a barrier film backsheet 61 and an absorbent body 62 therebetween. FIG. 9 shows a cross-section taken along line A—A of FIG. 8. Napkin 60 also comprises right and left longitudinally extending cuffs 63, 64 each of the cuffs being attached along their respective base portions 65, 66 to the right and left lateral sides 67, 68 of absorbent product, respectively, such that the distal ends 69, 70 of cuffs 63, 64 extend outward from right and left lateral sides 67, 68 of napkin 60. Perforated film cover 80 and barrier film backsheet 61 are attached to each other in a flange seal 71 and to base portions 65, 66 of cuffs 63, 64. Cuffs 63, 64 may be optionally longitudinally attached along their respective base portions 65, 66 to napkin 60: anywhere, between the respective lateral sides 67, 68 and the longitudinal centerline 81; along and above or below cover 80, but not including longitudinal centerline 81; along and above or below barrier film backsheet 61, including longitudinal centerline 81; in such fashion that ensures that cuffs 63, 64 extend at least outward from lateral sides 67, 68. Cuffs 63, 64 in this example may also be covered with a nonwoven 82 or with the perforated film such as cover 80 used in this invention. Cuffs may additionally be made of or contain in or on the cuffs other materials such as films, nonwovens and foam, the nonwoven or foam being preferably of a highloft material 83. Cuffs may also additionally contain elastic materials in or on the cuffs. Absorbent body 62 in FIGS. 8 and 9 has a roughly rectangular outline, and is thicker in the middle 73 than lateral sides 67, 68 or than the transverse ends 74, 75. Absorbent body 62 may have other outline shapes such as hourglass, dogbone or oval. Absorbent body 62, proceeding from the absorbent facing side of perforated film cover 80, further comprises a transfer layer 76 of a low density nonwoven material, an auxiliary absorbent layer 82 containing sphagnum moss and a main absorbent layer 78 such as of airlaid pulp. Napkin 60 also comprises positioning adhesive 78, on the garment side of barrier film backsheet 61, for attaching napkin 60 to an undergarment, positioning adhesive 78 being protected until use by a release paper 79. Absorbent body 62 may optionally contain as distinct layers, gradients, or as homogeneous dispersions, any or all of tissue, sphagnum moss and superabsorbent. Embodiments of napkins with cuffs such as are described herein are described in Patent Applications, commonly assigned and concurrently filed herewith, entitled, "Absorbent Article Having Compliant Cuffs" and "Stabilized Absorbent Article", herein incorporated in its entirety.

With continued reference to FIG. 8 and especially to FIG. 9, perforated cover 80 is further described, and differentiated from the unperturbed and unattached cover. Perforated cover 80, now having been appropriately adhered or tensioned, or adhered and tensioned, to absorbent body 62, exhibits perforate regions 58, being elevated with respect to nonperforate regions 59, the perforate regions 58 being further described and illustrated, but not restricted to the embodiments shown in FIGS. 4 and 5, as being comprised of a plurality of microholes, defined by a network of fiberlike elements; the fiberlike elements of cover 80, when attached to napkin 60, being raised above the surface of absorbent body 62 and at an elevation that is greater than that of non perforate regions 59.

Figure 10:
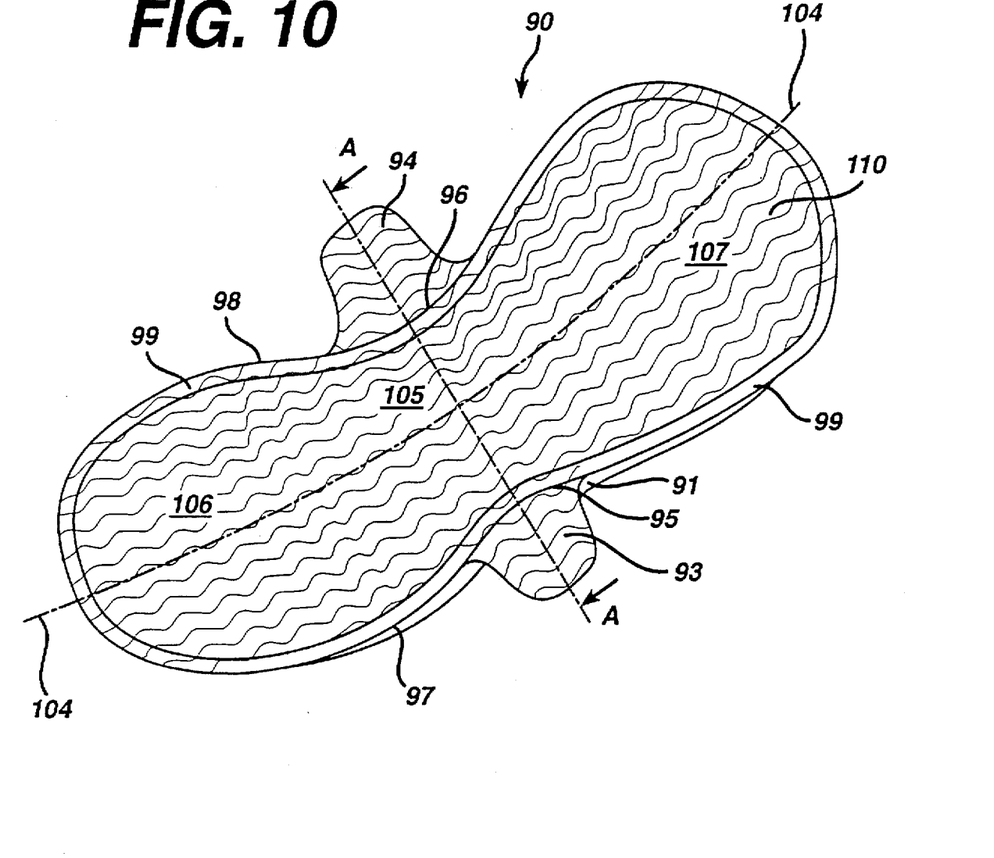
FIG. 10 is a perspective view of yet another sanitary napkin in accordance with this invention.
Figure 11:
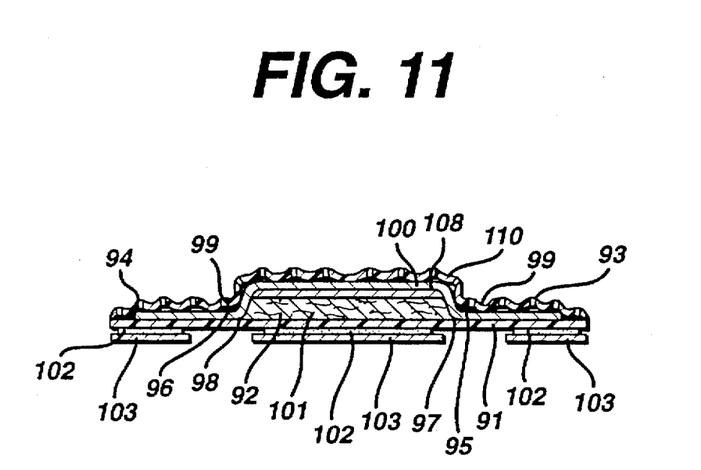
FIG. 11 is a cross-section of the sanitary napkin shown in FIG. 10.

FIG. 10 shows a perspective view of an absorbent product of this invention, a sanitary napkin 90 covered by a perforated film cover 110, a barrier film backsheet 91 and an absorbent body 92 therebetween. FIG. 11 shows a cross-section taken along line A—A of FIG. 10. The napkin also comprises right and left longitudinally extending wings or tabs 93, 94 each of the wings or tabs 93, 94 being attached along their respective base portions 95, 96 to the right and left lateral sides 97, 98 of sanitary napkin 90, respectively, such that the distal ends 99, 100 of wings or tabs 93, 95, extend outward from the right and left lateral sides 97, 98 of sanitary napkin 90. Perforated film cover 110 and barrier film backsheet 91 are attached to each other in a flange seal 99 and to the base portions of wings or tabs 93, 94. Wings or tabs 93, 94 in this example are also covered with perforated film cover 110 of this invention. The wings or tabs can optionally be attached to the sanitary napkin: longitudinally along and above or below the cover between and including the center of the napkin and adjacent the lateral sides; longitudinally anywhere along the lateral sides of the napkin; and longitudinally along and above or below the barrier film backsheet. Wings or tabs 93, 94 may be longitudinally attached, alternatively along their respective base portions 95, 96 anywhere, between the respective lateral sides 97, 98 and adjacent to but not including the longitudinal centerline 104; such that wings or tabs 93, 94 extend at least outward from lateral sides 97, 98. Absorbent body in FIGS. 10 and 11 has an hourglass outline and is thicker in the middle region 105 than the lateral sides or than the transverse ends 106, 107. Absorbent body 92 further comprises, proceeding from the absorbent facing side of perforated film cover 110, a transfer layer 108 made of a low density nonwoven material, an auxiliary absorbent layer 100 comprising sphagnum moss and a main absorbent layer 101 such as of airlaid pulp. Napkin 90 also comprises positioning adhesive 102, on the garment side of barrier film backsheet 91, for attaching napkin 90 and wings or tabs 93, 94 to an undergarment, positioning adhesive 102 being protected until use with a release paper 103. Absorbent body 92 may optionally contain as distinct layers, gradients, or as homogeneous dispersions, any or all of absorbents such as tissue, sphagnum moss and superabsorbent. Embodiments of napkins with wings such as are described herein are described in U.S. patent application, Ser. No. 198,809 entitled, "Body Conforming Absorbent Article" to McCoy et al, and commonly assigned, herein incorporated in its entirety by reference. With continued reference to FIG. 10 and especially to FIG. 11, perforated cover 110 is further described, and differentiated from the unperturbed and unattached cover. Perforated cover 110, now having been appropriately adhered or tensioned, or adhered and tensioned, to absorbent body 92, exhibits perforate regions 58, being elevated with respect to nonperforate regions 59, perforate regions 58 being further described and illustrated, but not restricted to the embodiments shown in FIGS. 4 and 5, as being comprised of a plurality of microholes, defined by a network of fiberlike elements the fiberlike elements of cover 110, when attached to napkin 90, being raised above the surface of absorbent body 92 and at an elevation that is greater than that of nonperforate regions 59.

It should be appreciated that in all absorbent products, such as that described in the foregoing Figures, the complexity of product topography and product profile will dictate different degrees of tension or relative relaxation of the permeable cover. Therefore, the positive elevational difference between perforate and nonperforate regions that is maintained may be due to attachment of the permeable cover to the product or to tensioning of the absorbent cover or to both attachment and tensioning.

In describing the present invention, certain embodiments have been used for purposes of illustration; however, other embodiments or modifications within the spirit and scope of the invention will readily occur to those skilled in the art after reading this disclosure. The invention isaccordingly not to be limited to the specific embodiments described and illustrated herein, but only in accordance with the appending claims.

What is claimed is:

1. An absorbent product comprised of a fluid permeable cover, a fluid impermeable barrier and an absorbent body therebetween, wherein the permeable cover is a microperforated fibrillated stretchable thermoplastic film which further comprises:

nonperforate regions; and perforate regions;

the perforate regions having a plurality of microholes defined by a network of fiberlike elements;

the perforate regions being, at least in part, at elevations that are higher than the nonperforate regions, wherein the perforate regions are caused to be at higher elevations than the nonperforate regions by means of tensioning the cover or by partly adhering the cover to the absorbent body or by combinations thereof.

2. The absorbent product of claim 1, wherein the fibrillated film is microembossed.

3. The absorbent product of claim 1, wherein the fibrillated film is smooth.

4. The absorbent product of claim 1, wherein the absorbent body is comprised of a transfer layer and an absorbent core.

5. The absorbent product of claim 4, wherein the transfer layer has a cover facing surface which is nonplanar.

6. The absorbent product of claim 5, wherein the absorbent core has a cover facing surface which is non planar.

7. The absorbent product of claim 5, wherein the absorbent core contains superabsorbent.

8. The absorbent product of claim 5, wherein the absorbent core contains sphagnum moss.

9. The absorbent product of claim 5, wherein the absorbent core contains wood pulp.

10. The absorbent product of claim 1, wherein the absorbent body is comprised of an absorbent core.

11. The absorbent product of claim 10, wherein the absorbent core has a cover facing surface which is nonplanar.

12. The absorbent product of claim 11, wherein the absorbent core contains superabsorbent.

13. The absorbent product of claim 11, wherein the absorbent core contains sphagnum moss.

14. The absorbent product of claim 11, wherein the absorbent core contains wood pulp.

15. The absorbent product of claim 1, wherein the nonperforate region is adhered to the absorbent body more completely than is the perforate region.

16. The absorbent product of claim 1, wherein the microholes have an area ranging from about 0.003 square mils to about 400 square mils.

17. The absorbent product of claim 1, wherein the microholes are provided in a pattern of distinct groups.

18. The absorbent product of claim 1, wherein the microholes are irregular in shape and are randomly distributed in the perforate regions.

19. The absorbent product of claim 1, wherein the microholes have a coefficient of variation of shape factor of at least 25%.

20. The absorbent product of claim 1, wherein the microholes have an average effective hydraulic diameter ranging from about 0.5 mils to about 50 mils.

21. The absorbent product of claim 1, wherein the microholes have a coefficient of variation of effective hydraulic diameter of at least 50%.

22. The absorbent product of claim 1, wherein the film has an open area ranging from about 1% to about 15%, the open area being provided at least in part by the microholes.

23. The absorbent product of claim 1, wherein the fiberlike el ments have lengths ranging from about 0.005 inch to about 0.05 inch.

24. The absorbent product of claim 1, wherein the fiberlike elements have widths ranging from about 0.001 inch to about 0.035.

25. The absorbent product of claim 1, wherein the fiberlike elements have thicknesses ranging from about 0.00025 inch to about 0.002 inch.

26. The absorbent product of claim 1, further comprising a plurality of secondary openings whose areas are larger than the areas of microholes.

27. An absorbent product comprised of a fluid permeable cover, a fluid impermeable barrier and an absorbent body therebetween, wherein the permeable cover is a microperforated fibrillated stretchable thermoplastic film which further comprises:
nonperforate regions; an
perforate regions;
the nonperforate regions being comprised of a series of valleys;
the perforate regions being a series of hills between the series of valleys, and being, at least in part, at elevations that are higher than the nonperforate regions; and
the hills having sides and comprising a plurality of microholes defined by a network of fiberlike elements and wherein the perforate regions are maintained at higher elevations than the nonperforate regions by means of tensioning the cover or by partly adhering the cover to the absorbent body or by combinations thereof.

28. The absorbent product of claim 27, wherein the nonperforate region is adhered to the absorbent body more completely than is the perforate region.

29. The absorbent product of claim 27, wherein the cover is tensioned and the nonperforate region is adhered to the absorbent body more completely than is the perforate region.

30. The absorbent product of claim 27, wherein at least a portion of the hills include a plurality of the microholes.

31. The absorbent product of claim 27, wherein the valleys and hills when viewed in plan, have sinusoidal-like configurations.

32. An absorbent product comprised of a fluid permeable cover, a fluid impermeable barrier and an absorbent body therebetween, wherein the permeable cover is a microperforated fibrillated stretchable thermoplastic film which further comprises:
nonperforate regions; and
perforate regions;
the nonperforate regions being comprised of a plurality of conelike structures, oriented generally downward with respect to the absorbent body;
the perforate regions being comprised of a plurality of hills between the conelike structures;
the hills comprising a plurality of microholes defined by a network of fiberlike elements;
the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

33. The absorbent product of claim 32, wherein the cover is tensioned with a force of about at least 2 grams/inch.

34. The absorbent product of claim 32, wherein the nonperforate region is adhered to the absorbent body more completely than is the perforate region.

35. The absorbent product of claim 32, wherein the cover is tensioned and the nonperforate region is adhered to the absorbent body more completely than is the perforate region.

36. An absorbent product comprised of a permeable cover, an impermeable barrier and an absorbent body therebetween, wherein the permeable cover is a microperforated fibrillated stretchable thermoplastic film which further comprises:
nonperforate regions; and
perforate regions;
the perforate regions being comprised of a plurality of microholes, the microholes being defined by a network of fiberlike elements and being arranged in a plurality of groups of microholes;
the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

37. The absorbent product of claim 36, wherein the nonperforate region is adhered to the absorbent body more completely than is the perforate region.

38. The absorbent product of claim 36, wherein the cover is tensioned and the nonperforate region is adhered to the absorbent body more completely than is the perforate region.

39. The absorbent product of claim 36, wherein the plurality of microholes comprises at least one row of microholes, the row of microholes having a strip of nonperforate material on either side thereof.

40. The absorbent product of claim 36, wherein the plurality of microholes comprises a plurality of rows of microholes and wherein the rows are separated from one another by strips of nonperforate material.

41. An absorbent product comprised of a permeable cover, an impermeable barrier and an absorbent body therebetween, wherein the permeable cover is a microperforated fibrillated stretchable thermoplastic film made from a pre-embossed film having a male side and a female side, the male side being the absorbent body facing side; wherein the microperforated film further comprises:
   nonperforate regions; and
   perforate regions;
      the perforate regions being comprised of a plurality of holes, the plurality of holes including first and second groups of holes; and the holes of the first group having a size greater than the holes of the second group, the holes of the first and second groups being defined by a network of fiberlike elements;
      the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

42. The absorbent product of claim 41, wherein the male side is treated with corona discharge and both male and female sides have surfactant applied thereto.

43. The absorbent product of claim 41, wherein the cover is tensioned with a force of about at least 2 grams/inch.

44. The absorbent product of claim 41, wherein the nonperforate region is adhered to the absorbent body more completely than is the perforate region.

45. The absorbent product of claim 41, wherein the cover is tensioned and the nonperforate region is adhered to the absorbent body more completely than is the perforate region.

46. A sanitary napkin, having a pair of lateral sides, a pair of transverse ends and a central portion, the sanitary napkin comprising:
   a perforated film cover;
   a barrier film backsheet;
   an absorbent body therebetween;
   the sanitary napkin having, within the central portion, a pair of deeply embossed channels, the channels including the perforated cover and at least part of the absorbent body;
   the absorbent body being thicker in the central portion, and tapering to less thickness from the central portion toward the transverse ends; and
   wherein the permeable cover is a microperforated fibrillated stretchable thermoplastic film which further comprises:
      nonperforate regions; and
      perforate regions;
         the perforate regions having a plurality of holes, comprising large holes or small holes or combinations thereof, the plurality of holes being defined by a network of fiberlike elements;
         the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

47. A sanitary napkin, having a longitudinal centerline, a pair of lateral sides and a pair of transverse ends, the absorbent product comprising:
   perforated film cover;
   a barrier film backsheet;
   an absorbent body therebetween; and
   a pair of cuffs, each having a base portion and a distal end, each cuff longitudinally extending and attached, along its respective base portion, to one or a combination of the perforated cover, barrier film backsheet and respective lateral side; such that the distal ends of the cuffs extend at least outward from the lateral sides of the absorbent article; and
   wherein the permeable cover is a microperforated fibrillated stretchable thermoplastic film which further comprises:
      nonperforate regions; and
      perforate regions;
         the perforate regions having a plurality of holes, comprising large holes or small holes or combinations thereof, the plurality of holes being defined by a network of fiberlike elements;
         the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

48. A sanitary napkin, having a longitudinal centerline, a pair of lateral sides and a pair of transverse ends, the absorbent product comprising:
   a perforated film cover;
   a barrier film backsheet;
   an absorbent body therebetween; and
   a pair of wings, each having a base portion and a distal end, each wing longitudinally extending and attached, along its respective base portion, to one or a combination of the perforated cover, barrier film backsheet and respective lateral side; such that the distal ends of the wings extend at least outward from the lateral sides of the absorbent article; and
   herein the permeable cover is a microperforated fibrillated stretchable thermoplastic film which further comprises:
      nonperforate regions; and
      perforate regions;
         the perforate regions having a plurality of holes, comprising large holes or small holes or combinations thereof, the plurality of holes being defined by a network of fiberlike elements;
         the perforate regions being, at least in part, at elevations that are higher than the nonperforate regions and wherein the perforate regions are maintained at higher elevations than the nonperforate regions by means of tensioning the cover or by partly adhering the cover to the absorbent body or by combinations thereof.

* * * * *

UNITED STATES PATENT AND TRADEMARK OFFICE
CERTIFICATE OF CORRECTION

PATENT NO. : 5,895,380
DATED : April 20, 1999
INVENTOR(S) : Mordechai Turi, Pramod S. Mavinkurve, Linda J. McKeekin It is certified that error appears in the above-indentified patent and that said Letters Patent is hereby corrected as shown below:

On the title page;

Inventors: (75) Linda J. McKeekin SHOULD BE Linda J. McMeekin

Signed and Sealed this

Twenty-fourth Day of August, 1999

Attest:

Q. TODD DICKINSON

*Attesting Officer*    *Acting Commissioner of Patents and Trademarks*